(12) United States Patent
Smith et al.

(10) Patent No.: US 9,498,238 B2
(45) Date of Patent: Nov. 22, 2016

(54) TISSUE RESECTION SNARES

(71) Applicant: BOSTON SCIENTIFIC SCIMED, INC., Maple Grove, MN (US)

(72) Inventors: Paul Smith, Smithfield, RI (US); Samuel Raybin, Marlborough, MA (US); Naroun Suon, Lawrence, MA (US); Larry Stanton, Burlington, MA (US); Robert DeVries, Northboro, MA (US); John Golden, Norton, MA (US); Daniel Lang, North Attleboro, MA (US); Devon Amos, Ayer, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 127 days.

(21) Appl. No.: 14/211,675

(22) Filed: Mar. 14, 2014

(65) Prior Publication Data
US 2014/0276911 A1    Sep. 18, 2014

Related U.S. Application Data

(60) Provisional application No. 61/790,717, filed on Mar. 15, 2013.

(51) Int. Cl.
 *A61B 17/221* (2006.01)
 *A61B 17/3205* (2006.01)
 *A61B 17/00* (2006.01)

(52) U.S. Cl.
 CPC ....... *A61B 17/221* (2013.01); *A61B 17/32056* (2013.01); *A61B 2017/00858* (2013.01)

(58) Field of Classification Search
 CPC ................. A61B 17/221; A61B 2017/00358; A61B 17/32056; A61B 2017/2212; A61B 2017/2217; A61B 2017/320733
 USPC ................. 606/110, 111, 112, 113, 114, 127
 See application file for complete search history.

(56) References Cited

U.S. PATENT DOCUMENTS

| 3,828,790 A | 8/1974 | Curtiss et al. |
| 3,955,578 A | 5/1976 | Chamness et al. |
| 5,387,219 A | 2/1995 | Rappe |

(Continued)

FOREIGN PATENT DOCUMENTS

| JP | 200271146 | 10/2000 |
| JP | 2000271146 A | * 10/2000 |

(Continued)

OTHER PUBLICATIONS

International Search Report and Written Opinion for corresponding International Application No. PCT/US2014/028423 mailed on Sep. 15, 2014, (20 pages).

*Primary Examiner* — Katrina Stransky
(74) *Attorney, Agent, or Firm* — Bookoff McAndrews, PLLC

(57) ABSTRACT

A tissue resection device for resecting tissue from a target site within a patient's body. The device includes an elongate shaft having a proximal end and a distal end. An actuation member extends partially through the shaft, and reciprocates within the shaft between a retracted position and an extended position. Multiple snare wires extend through the actuation member, and emerge outwards from a distal portion of the actuation member. The snare wires cooperate and join to form a snare loop, which engages the tissue intended to be resected. The snare loop is configured to enhance friction while engaging the tissue, to resect the tissue.

18 Claims, 9 Drawing Sheets

(56) References Cited

U.S. PATENT DOCUMENTS

| | | |
|---|---|---|
| 5,417,684 A | 5/1995 | Jackson et al. |
| 5,417,697 A | 5/1995 | Wilk et al. |
| 5,782,839 A | 7/1998 | Hart et al. |
| 5,782,840 A * | 7/1998 | Nakao .................... A61B 18/14 606/110 |
| 6,123,665 A | 9/2000 | Kawano |
| 6,183,482 B1 | 2/2001 | Bates et al. |
| 7,559,934 B2 | 7/2009 | Teague et al. |
| 7,608,087 B1 | 10/2009 | Addis |
| 7,875,038 B2 | 1/2011 | Que et al. |
| 8,157,811 B2 | 4/2012 | Shinozuka et al. |
| 8,157,818 B2 | 4/2012 | Gartner et al. |
| 2004/0092953 A1 | 5/2004 | Salameh et al. |
| 2004/0199200 A1 * | 10/2004 | Teague ................ A61B 17/221 606/200 |
| 2008/0221587 A1 * | 9/2008 | Schwartz ............. A61B 17/221 606/113 |
| 2008/0234693 A1 | 9/2008 | Stefanchik |
| 2012/0172662 A1 * | 7/2012 | Kappel ................ A61B 17/221 600/104 |

FOREIGN PATENT DOCUMENTS

| | | |
|---|---|---|
| JP | 2001258892 | 9/2001 |
| WO | WO 93/21845 | 11/1993 |

* cited by examiner

TISSUE RESECTION SNARES

CROSS-REFERENCE TO RELATED APPLICATIONS

This application claims the benefit of priority from U.S. Provisional Application No. 61/790,717, filed on Mar. 15, 2013, the entirety of which is incorporated by reference herein.

FIELD OF THE DISCLOSURE

Embodiments of the present disclosure generally relate to medical devices and procedures. In particular, embodiments of the present disclosure relate to medical devices for resecting and collecting tissue from a portion of a patient's body.

BACKGROUND OF THE DISCLOSURE

Medical devices, such as endoscopes or other suitable introduction sheaths are employed for a variety of diagnostic and surgical procedures, such as laparoscopy, arthroscopy, gynoscopy, thoracoscopy, and cystoscopy, etc. Many of these procedures are carried out for purposes of tissue resection, which generally includes removal of tissue of an organ or a gland to treat tumors, infestations, and the like. In particular, such procedures may be carried out by inserting an introduction sheath into a patient's body through a surgical incision, or via natural anatomical orifices (e.g., mouth, vagina, and/or rectum), and performing the procedure or operation.

The tissue resection operation may be performed during several medical procedures, which may require removal and/or carving away of tissue or tissue layers from a patient's body. Specifically, this operation may include removal of tissue overlaying and/or adjacent a region infected by cancerous tumors and/or other infections. On many occasions, tissue resection may be performed through a process widely known and referred to as electro-resectioning, which may be carried out through an electro-cautery probe.

Typically, removal of tissue through methods such as electro-resectioning includes application of a cauterization voltage to a related electrode, and steering it into a region within the patient's body. This may be enabled through known methods, which may target ablation of a tissue from, or adjacent to an area.

Snares, in particular, have been used in many medical procedures, including Endoscopic Mucosal Resection (EMR) and Endoscopic Sub-mucosal Resection (ESR), Polypectomy, Mucosectomy, etc., for resecting tissue from a target site. A snare device generally includes a snare loop formed by snare wires, which engages the tissue intended to be resected. The snare loop is controlled and operated at a proximal end of the device through a suitable actuating mechanism. However, in many conventional snare devices, the snare loop has a tendency to slip off the tissue that is desired to be ensnared. During endoscopic procedures, this problem may be partially addressed by applying a downward force with the endoscope to improve snare traction. However, such an applied force may create torsion in snare wires, and hence, may tend to rotate the snare loop. This may deflect the snare loop from the plane of the layer of tissue, and make the tissue resection difficult. Further, the snare wires, during packing, may have in-built torsional forces, which may cause unpredictable rotation of the snare loop during its engagement with the tissue.

In many Endoscopic Mucosal Resection (EMR) techniques, the submucosal layer at/adjacent to the target site is treated with a saline solution, which functions to lift the mucosal layer, forming a bleb. The bleb may facilitate easy access to, and visualization of the lesion, and may create a protective barrier at the muscularis layer. However, formation of the bleb may create tension in the mucosa surrounding the lesion, and this may make the process of snaring even more difficult.

Therefore, there remains a need for a mechanism and a method that can improve ensnarement of tissue intended to be resected, during certain medical procedures.

The present disclosure is directly to overcome the shortcomings mentioned above and other shortcomings in the art.

SUMMARY OF THE DISCLOSURE

The present disclosure provides a medical device, as well as a medical procedure using the medical device, for resecting a tissue from a target site within a patient's body.

In one aspect, the present disclosure provides a tissue resection device for resecting tissue from a region within a patient's body. The device includes an elongate shaft having a proximal end and a distal end. An actuation member extends partially through the elongate shaft, and is capable of reciprocating through the shaft between a retracted position and a fully extended position. A snare wire passes through a lumen of the actuation member, and extends outward from a distal portion of the actuation member. Emerging outwards from the distal portion, the snare wire forms a snare loop, which engages with tissue desired to be resected from a target site. The snare loop can be extended to engage the tissue desired to be resected. Once the tissue is resected, the snare loop can be retracted into the actuation member, to completely remove the resected tissue. The reciprocation of the actuation member between its fully extended position and its retracted position causes movement of the snare loop between its extended orientation, and its retracted orientation within the snare loop.

In another aspect, the present disclosure provides a method for resecting tissue from a portion of a patient's body. The method includes inserting a medical device partially into a lumen of the body, and positioning a distal portion of the device proximal to the portion of the body. The medical device includes an elongate shaft having a proximal end and a distal end, and an actuation member extending partially through the elongate shaft. One or more snare wires pass through a lumen of the actuation member. The snare wires are extended outwards from a distal portion of the actuation member. A snare loop is formed of the extending snare wires, and the snare loop is engaged with the tissue intended to be resected from the portion of the body. The actuation member is moved to bring the snare loop in an extended orientation, for resecting the tissue through the snare loop. Once the tissue is resected, the snare loop is retracted into the actuation member, to fully remove the resected tissue.

Additional objects and advantages of the described embodiments will be set forth in part in the description that follows, and in part will be understood from the description, or, may be learned by practicing the disclosure. The objects and/or advantages of the disclosure will be realized and attained by way of the elements and combinations particularly pointed out in the appended claims.

It is to be understood that both the foregoing general description and the following detailed description are exemplary and explanatory only, and are not restrictive of the described embodiments, as claimed.

BRIEF DESCRIPTION OF THE DRAWINGS

The accompanying drawings, which are incorporated in, and constitute a part of this specification, illustrate exemplary embodiments of the present disclosure and, together with the description, serve to explain the principles of the disclosure.

DESCRIPTION OF THE EMBODIMENTS

Reference will now be made in detail to embodiments of the present disclosure, examples of which is illustrated in the accompanying drawings. Wherever possible, the same reference numbers will be used throughout the drawings to refer to the same or like parts.

Embodiments of the present disclosure may relate to devices used in medical procedures like Endoscopic Mucosal Resection (EMR), Endoscopic Submucosal Dissection (ESD), polypectomy and mucosectomy, etc. More particularly, embodiments of the present disclosure are directed to medical procedures using snares to ensnare tissue from a target site within a patient's body, where the engagement of a snare loop while being associated with the tissue is enhanced by suitable structures cooperating with each other, when the medical device is operated. The medical device may include an elongate shaft having a proximal end and a distal end. An actuation member may extend partially through the elongate shaft, and may reciprocate (i.e., move back and forth) through the shaft. A proximal end of the elongate shaft may be operably connected to an actuating mechanism, and a distal end may be operably coupled to a suitable end-effector. The end-effector may be a snare loop, which may be controlled and manipulated by an operator/surgeon/physician, using the actuating mechanism at the proximal end of the elongate shaft, while performing the medical procedure. The end-effector engages the tissue intended to be resected through suitable structures cooperating with each other, to enhance friction and to facilitate smooth resecting, during the engagement of the snare loop with the tissue. The integral components of medical device of the present disclosure will be explained in further details hereinafter, in conjunction with the figures to follow.

As part of the disclosure, mechanisms may facilitate the connection and disconnection of snare loops having different appropriate structures, to the distal portion of the medical device, as will be explained through different embodiments of the present disclosure hereinafter.

Various shapes of the end-effector can be utilized for the snare loop, for example, these can be circular, elliptical, ovular, polygonal, and irregular in shape, etc., while engaging the tissue, and such shapes are intended to be within the scope of the present disclosure. Various configurations of the medical device's articulation, structure, and function are described in the embodiments of the disclosure. Further, wherever used in the disclosure, "distal" generally refers to a position or direction away from a user (i.e., the surgeon, physician, etc.), and "proximal" generally refers to a position or direction opposite the "distal" direction, and hence, closer to the user (i.e., towards the user).

Exemplary Embodiments

Figure 1A:
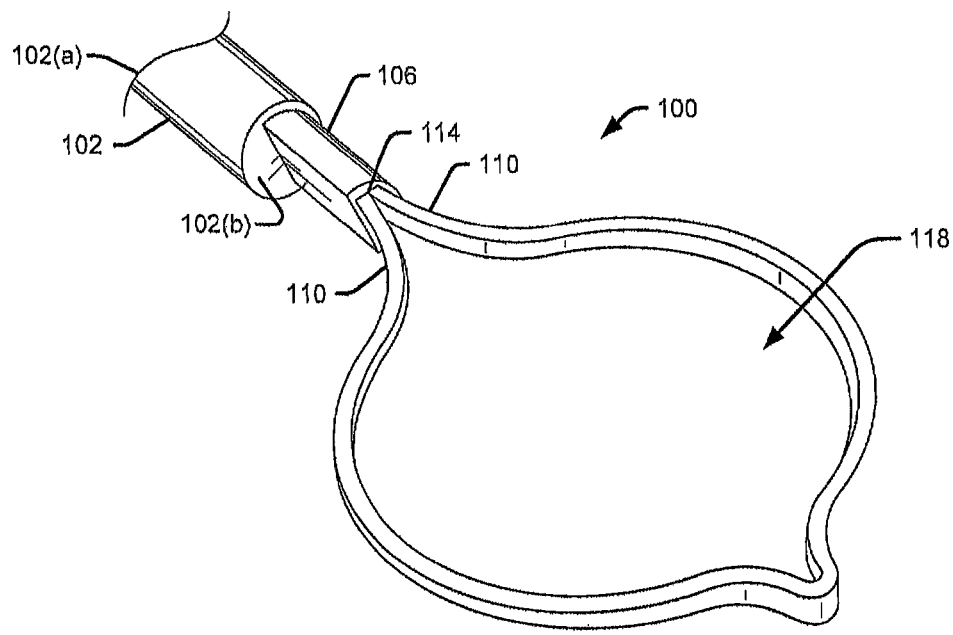
FIGS. 1A-1C illustrate various perspective views of a medical device for resecting tissue in accordance with an embodiment of the present disclosure.
Figure 1B:
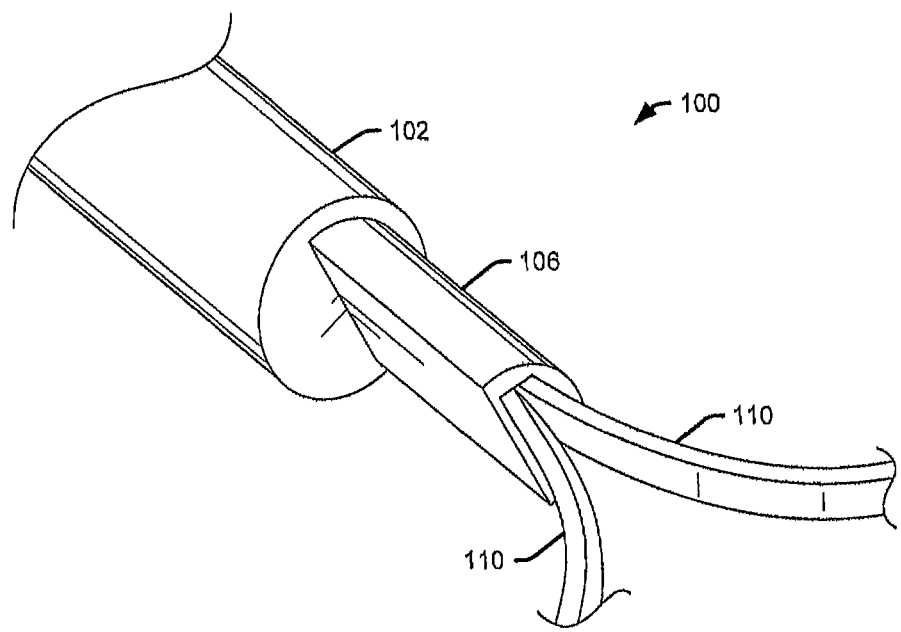
Figure 1C:
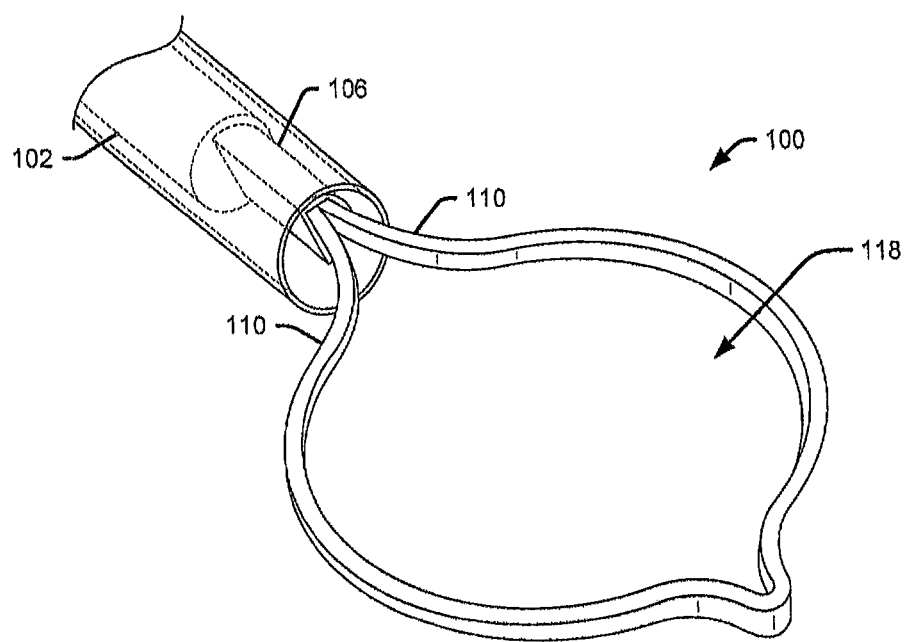

FIGS. 1A-1C show different perspective views of a medical device for resecting tissue from a target site within a patient's body, in accordance with an embodiment of the present disclosure.

As shown in FIG. 1A, a medical device 100 may include an elongate shaft 102, having a proximal end 102 (*a*) and a distal end 102 (*b*). The elongate shaft 102 may be inserted into a lumen of a patient's body, to access a target site whereon a medical procedure is intended to be performed. The proximal end 102 (*a*) may be connected to a suitable actuation mechanism (not shown), for operating the medical device. The actuating mechanism may be any appropriate mechanism for controlling and operating the components of the medical device 100, to enable resection of tissue using the medical device. In an embodiment, the actuating mechanism may be a handle, configured to be driven either manually, or through a pneumatic, hydraulic or an electro-mechanical mechanisms.

An actuation member 106 may extend partially through the elongate shaft 102, and further, may extend outwards from the distal end 102 (*b*) of the elongate shaft. The actuation member 106 may reciprocate through or within a lumen of the shaft 102, between a retracted position and a fully extended position. While being in the fully extended position, a distal portion of the actuation member 106 may extend out from the distal end 102 (*b*). In the retracted position, the actuation member 106 may be capable of being fully retracted and contained within the shaft 102. Further, the reciprocation of the actuation member 106 through the shaft 102 may be facilitated through the actuating mechanism provided at a proximal portion of the medical device, as aforementioned.

Figure 6:
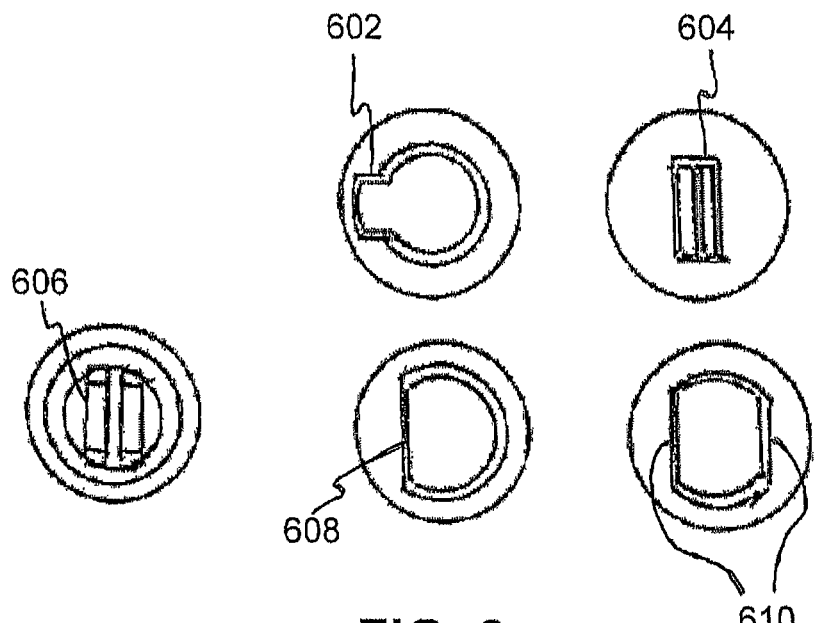
FIG. 6 shows cross-sectional views of exemplary keying mechanisms for orienting a snare loop, in accordance with another embodiment of the disclosure.
Figure 7:
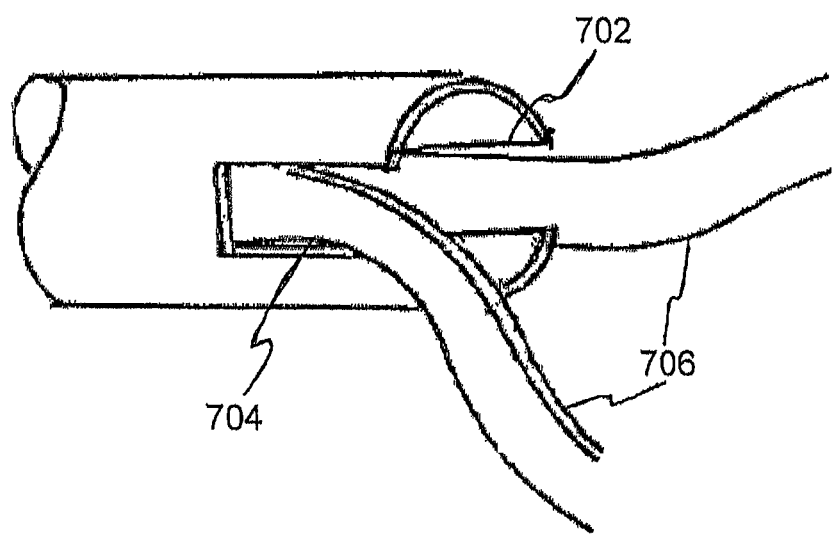
FIG. 7 shows a perspective view of a medical device for resecting tissue, in accordance with another embodiment of the disclosure.
Figure 8:
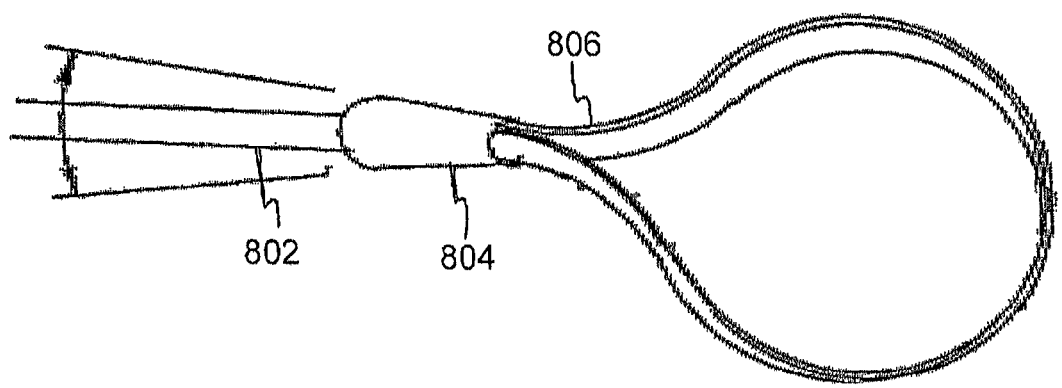
FIG. 8 shows a perspective view of a medical device for resecting tissue, in accordance with another embodiment of the disclosure.

Though currently shown as being of a semi-circular cross-section, the actuation member 106 may also be of any other suitable cross-section/structure, e.g., a polygonal, regular or irregular structure, etc. Further, the shape of the elongate shaft 102 may change depending on the shape of the actuation member 106, to facilitate accommodation of the actuation member 106 into the shaft 102. Various other mechanisms may be used to urge snare wires 110 into an orientation that causes desired orientation of snare loop 118. That is, although FIGS. 1A and 1B depict actuation member 106 as being semi-circular and radially-orienting relative to a similarly shaped aperture of shaft 102, any other shape may be used. For example, FIG. 6 depicts other exemplary cross-sectional shapes of an actuation member, such as one having a key 602, a rectangle 604, two or more separated rectangles 606, a semi-circle 608, and/or two opposed flat faces 610. Thus, snare wires 110, actuation element 106, and shaft 102 may share any desired regular or irregular cross-sectional shape that urges them into a desired radial orientation relative to each other. In one embodiment, as shown in FIG. 7, a shaft 102 and/or actuation member 106 may each include one or more slits 702, 704, which allow snare wires 706 to extend through the slits and control radial orientation of the snare wires. In yet another embodiment, as shown in FIG. 8, a tapered lock 804 may be disposed over a shaft 802, such as at or around an interface between shaft 802 and snare wires 806. Tapered lock 804 may be shaped, for example to include an angled or tapered inner aperture, such that movement of the tapered lock 804 in distal direction causes snare wires 806 to be pressed together, to resist rotation, and/or to be oriented in a desired radial orientation. In one embodiment, an inner lumen of a tapered lock 804 may include any of the cross-sectional features described with respect to FIG. 6.

Multiple snare wires 110 may be provided to pass through the actuation member 106, and may extend out distally, to form a snare loop 118. Specifically the distal ends of the snare wires 110 may cooperate to join, and form the snare loop 118. As shown, the snare wires 110 may have a flattened shape, with a generally rectangular cross-section. When these snare wires cooperate to form the snare loop 118, they may orient themselves substantially perpendicular to the plane of the layer of tissue that the snare loop 118 engages with. Further, a proximal end of each of the snare wires 110 may be anchored to an interior portion of the actuation member 106. Any suitable mechanisms may be used to secure the proximal ends of the snare wires 110, including sealing or adhesively bonding the proximal ends to the interior portion of the actuation member 106. When anchored at their proximal ends to the interior portion of the actuation member 106, the snare wires 110 may be maintained in a fixed orientation relative to the layer of tissue, which may prevent these wires from rotating, due to any torsional forces developing therein. The actuation member 106 may act as an anti-torsion element for the snare wires 110. Further, since the snare wires remain in a relatively constant plane, the frictional engagement of the snare loop 118 with the tissue can be enhanced, and this mitigates the tendency of the snare loop 118 to slip off the target site.

To allow passage of the snare wires 110 through the actuation member 106, one or more openings 114 may be provided at a distal end of the actuation member 106, as shown. The size of such openings may depend on the dimensions of the snare wires 110. In an embodiment, the openings 114 may be designed to have an aperture that may assist in increasing vertical stiffness of the snare wires 110, while they pass through the openings, and eventually, engage the tissue. Specifically, the openings 114 may have a cross-section small enough to prevent the snare wires 110 from rotating therein, while passing through, and this may further ensure that the plane of orientation of the snare loop 118, while engaging the tissue remains substantially constant. This provides a high stiffness to the snare wires 110 while they engage the tissue, and may substantially reduce the tendency of the snare loop 118 to slip off from the tissue layer.

It is contemplated that a single snare wire 110 may be provided to pass through the actuation member 106, and extend outwards, to form the snare loop 118. That wire may have a similar structure, i.e., a flattened surface with a rectangular cross-section, and while engaging the tissue, the wire may orient itself substantially perpendicular to the plane of the tissue. Further, the ends of that wire may be anchored to an interior portion of the actuation member 106, to prevent the wire from rotating and changing its orientation while engaging the tissue.

To facilitate resection of the tissue through the snare loop 118, the actuation mechanism disposed at a proximal portion of the medical device 100, may be used to control the snare wires 110, and hence, the snare loop 118. Once the intended tissue has been resected, the snare loop 118 can be collapsed by retracting the snare wires 110 into the actuation member 106, to completely remove the resected tissue. In an embodiment, with the movement of the actuation member 106 distally, along the longitudinal axis of the elongate shaft 102, the snare wires 110 may simultaneously move in response, and this may affect the transition of the snare loop from its retracted position within the elongate shaft 102, into an expanded orientation. In a fully extended position of the actuation member 106 and the snare wires 110, in the direction outwards and away from the elongate shaft 102, the snare wires 110 may be completely drawn outwards, bringing the snare loop 118 into the expanded orientation. Further, in a similar manner, movement of the actuation member 106 and the snare wires 110 proximally, into the elongate shaft 102, may retract the snare wires 110 into the elongate shaft 102, and thus, may bring the snare loop 118 into its retracted position within the elongate shaft. Further, as mentioned earlier, the reciprocation of the actuation member 106 through the lumen of the elongate shaft 102 may be controlled through the actuation mechanism (not shown), disposed at the proximal portion of the medical device 100.

FIG. 1B shows a perspective partial view of the medical device 100, with the snare wires 110 extending outwards from the actuation member 106, and the actuation member 106 extending out from the elongate shaft 102, in an extended position.

FIG. 1C shows another perspective view of the medical device 100 of the present disclosure, where the snare loop 118 is in an expanded orientation, and is ready to engage the tissue intended to be resected. As shown, in this configuration, the actuation member 106 is retracted inward into the elongate shaft 102. It is contemplated that the elongate shaft 102 may have a sufficient longitudinal length to completely accommodate the actuation member 106 in its retracted position.

The actuation member 106 may be made of a conductive material, to allow passage of electric current through it, and for adapting it to serve as an electrical path for cautery cutting of the resected tissue. The actuation member 106 may be made of any suitable conductive material, including a metallic conductor, for example, aluminum, copper, etc., or a suitable conductive metallic alloy. A suitable current supplying source may transfer electric charge through the actuation member 106, to establish a flow of current through the actuation member 106. The current may be transferred to the snare loop 118, through the snare wires 110, to facilitate hot cautery cutting of the tissue resected by the snare loop 118.

Figure 2:
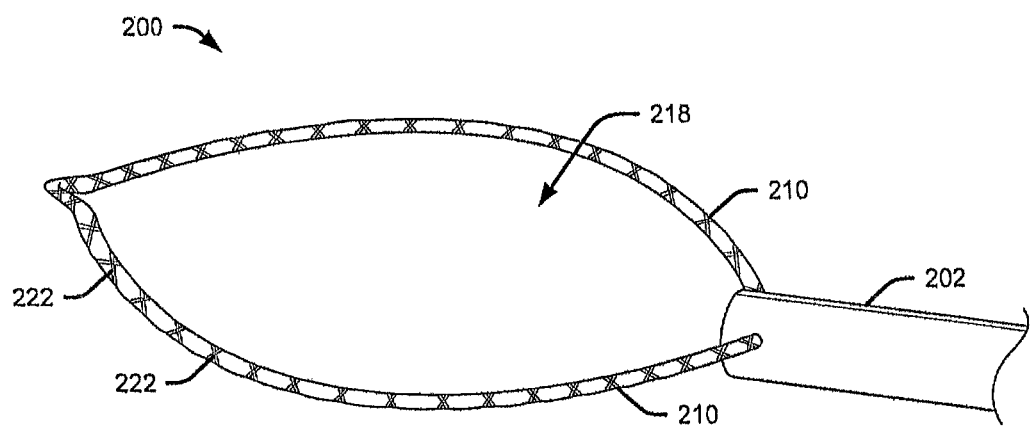
FIG. 2 is a perspective view of a medical device, according to another embodiment of the present disclosure.

FIG. 2 shows a perspective view of a medical device 200 for resecting tissue, from a target site within a patient's body, according to another embodiment of the present disclosure. As shown, a set of snare wires 210 may extend outward from the elongate shaft 202, to form a snare loop 218 configured to overlay and engage tissue. The method or mechanism for extending the snare wires 210 outward from the actuation member (though not shown herein); the provisions for incorporating the snare wires and retracting them into the actuation member; and the mechanism for facilitating reciprocation of the actuation member through the elongate shaft 202 may be similar to those described above in conjunction with FIG. 1A-1C. Hence, these will not be described in detail herein, to avoid unnecessary repetition.

The snare wires 210 may have any suitable cross-section, including a round, or an ovular cross-section. In the illustrated embodiment, the snare wires 210 may be designed to substantially increase the gripping potential of the snare loop 218, on engagement with the tissue. This is achieved by providing suitable structural modifications around the outer surface of the snare wires 210, in order to increase traction between the snare wires 210 and the tissue. Specifically, a gripping surface geometry for the snare loop 218 may be achieved by providing structural surface modifications 222, over portions of the snare wires 210 constituting the snare loop 218. The modifications 222 may be striations, knurls, grooves or indentations extending either partially across the peripheral surface of the snare loop 218, or extending across the entire length of the snare loop 218. Further, the modifications 222 may also be in the form of protrusions extending over the peripheral surface of the snare loop 218, to increase traction or friction between the snare loop 218 and the underlying tissue. Provision of the modifications 222 may substantially increase the gripping capacity of the snare loop 218 over the tissue, and ease pinching of the tissue during resection. The snare loop 218 may also have an irregular surface pattern.

FIGS. 3A-3D illustrate a medical device for resecting tissue according to another embodiment of the present disclosure.

Figure 3A:
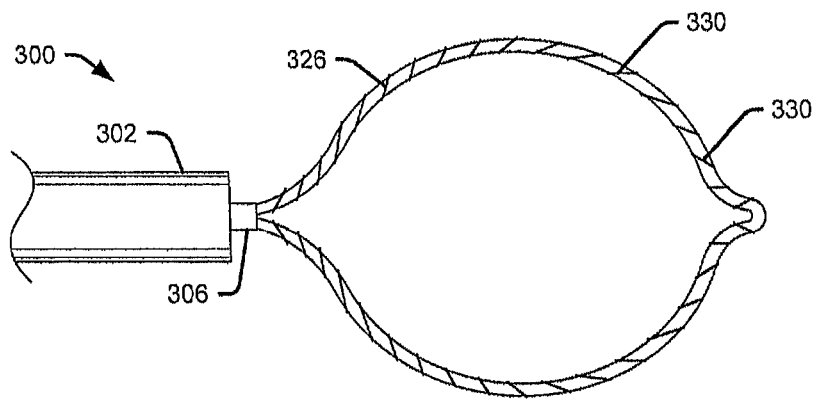
FIGS. 3A-3D illustrate various perspective views of a medical device for resecting tissue, in accordance with another embodiment of the present disclosure.

As shown in FIG. 3A, a medical device 302 includes an elongate shaft 300 having an actuation member 306 contained therein, which reciprocates through the shaft 302 between a fully extended position and a retracted position. Multiple snare wires may cooperate to form a snare loop 318, which engages with an underlying tissue intended to be resected. In the illustrated embodiment, a substantially helical structure 326 may surround the snare loop 318, and may extend across the entire length of the snare loop 318. However, the helical structure 326 may also only partially cover the length of the snare loop 318. The structure 326 may be formed by one or more different wire springs 330 coiled around the snare loop 318, and joined to form a partial or continuous helix. The wire springs 330 may be spaced apart appropriately, defining a pitch for the helical structure 326, and this pitch may change when the snare loop 318 stretches or contracts, due to movement of the actuation member 306 residing partially within the elongate shaft 302. Specifically, when the snare loop 318 is in a fully expanded orientation over the tissue, the spacing between the wire springs 330 may be maximized. When the snare loop 318 is retracted inwards, into the actuation member 306, the spacing between the wire springs 330 (i.e., the pitch of the helical structure 330) may decrease in response to retraction, and the adjacently placed wire springs 326 may pinch the underlying tissue by moving closer to each other. Arranging the wire springs 330 over the snare loop 318, to create the substantially helical structure 326, also may prevent slippage of the snare loop 318 over the underlying tissue. The wire springs 330 may have an outer surface sufficiently rough, i.e., to increase traction, while engaging the tissue, thus, avoiding slippage. It is contemplated that the substantial helical structure 326 may include a wrapped or coiled wire that has an irregular and/or varying pitch between the coils.

Figure 3B:
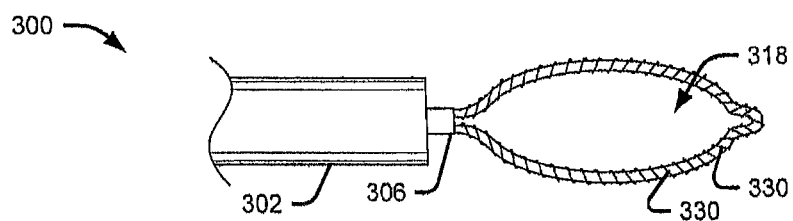

FIG. 3B shows the medical device 300, with the helical structure 326 being in a compressed state, due to partial retraction of the snare loop 318 into the actuation member residing in the elongate shaft 302. As compared to the arrangement shown in FIG. 3A, the wire springs 330 may be more closely spaced, and are capable of pinching the underlying tissue along different portions. To facilitate compression of the wire springs 330, they may be made of any suitable conventional flexible material.

Figure 3C:
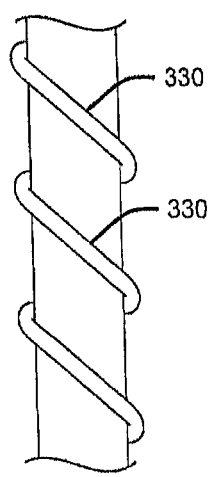
Figure 3D:
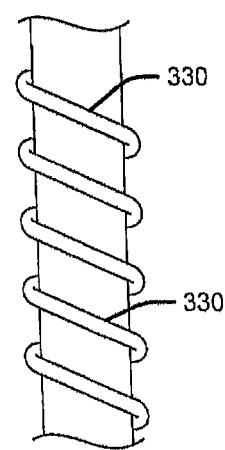

FIGS. 3C & 3D are partial views showing the wire springs 330 coiled around the snare loop 318. Specifically, FIG. 3C and FIG. 3D show an exemplary decrease in the pitch of the helical structure 326, due to compression of the wire springs 330.

Figure 3E:
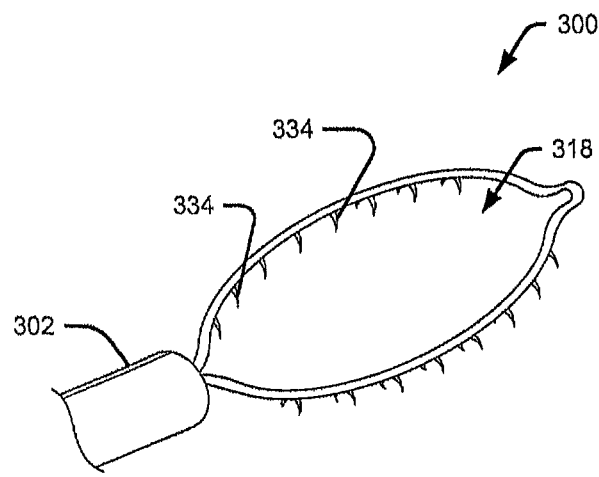
FIGS. 3E and 3F show perspective views of a medical device, according to another embodiment of the present disclosure.

FIG. 3E illustrates another embodiment where a pinching mechanism may be provided across the length of the snare loop 318, in order to pinch tissue, when the snare loop 318 engages the tissue. In this case, the pinching mechanism may include pinching structures 334 having pairs of pincer elements or hooks positioned over different portions of the peripheral structure of the snare loop 318, to grab the tissue at different locations.

Figure 3F:
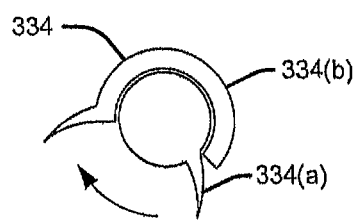

The pinching structure 334 is now explained in conjunction with a cross-section view of the snare loop 318 shown in FIG. 3F. As shown, the pinching structure may include a pair of pincer elements 334(*a*) and 334(*b*). An inner pincer element 334 (*a*) may be capable of rotating with respect to an outer pincer element 334 (*b*). Once the inner pincer element 334 (*a*) has rotated substantially, a portion of the underlying tissue is grabbed between the two pincer elements. In some cases, both the pincer elements 334 (*a*) and 334 (*b*) may also rotate toward each other, to quickly grab the tissue. It is contemplated that any number of pincer elements may be disposed on the snare loop 318.

To facilitate rotation of the inner pincer elements 334 (*a*) with respect to the outer pincer elements 334 (*b*), a suitable mechanism may be coupled to the pinching structure 334. In one embodiment, an electrical actuating mechanism may be disposed at the proximal portion of the elongate shaft 302, which may be coupled to each of the inner pincer elements 334 (*a*), to facilitate their rotation with respect to the outer pincer elements 334 (*b*). The outer pincer elements 334 (*b*) may be magnetized to create a magnetic field around the inner pincer elements 334 (*a*). The electrical actuating mechanism may pass an electric current through the inner pincer element 334 (*a*), and being placed in the magnetic field of the outer pincer element 334 (*b*), the inner pincer element 334 (*a*) may experience a torque, and rotate toward the outer pincer element 334 (*b*). Further, the pinching structure may also extend only partially across the length of the snare loop 318, in order to facilitate grabbing of the tissue at specific desired portions.

Figure 4A:
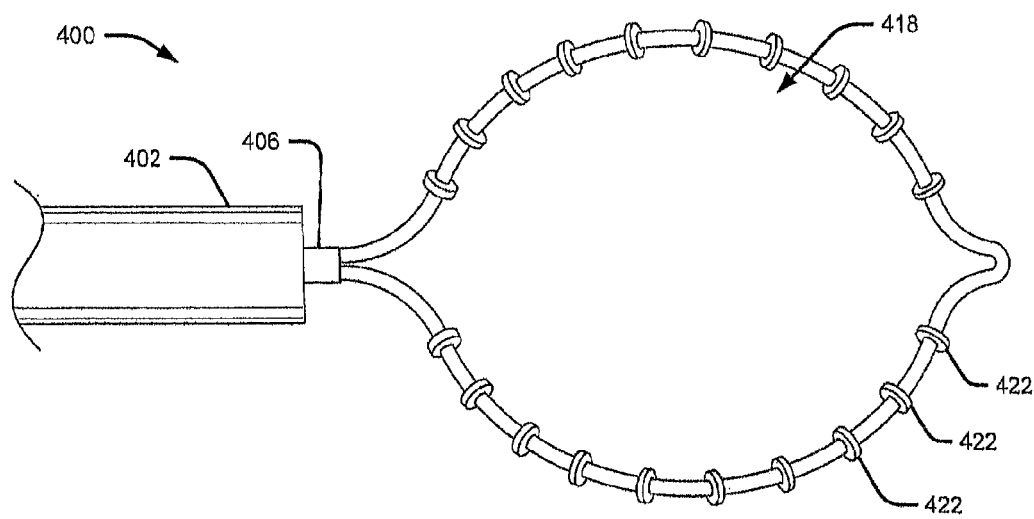
FIGS. 4A-4C illustrate various perspective views of a medical device for resecting tissue from a target site within a patient's body, in accordance with another embodiment of the present disclosure.
Figure 4B:
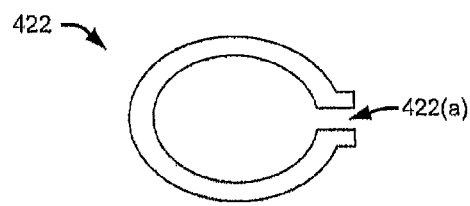
Figure 4C:
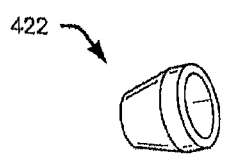

FIGS. 4A-4C illustrate views of a medical device 400 for resecting tissue, in accordance with another embodiment of the present disclosure.

FIG. 4A shows a perspective view of the medical device 400. An elongate shaft 402 incorporates an actuation member 406 extending outwards distally, from the shaft 402. In a manner similar to the one or more previous embodiments of the disclosure, multiple snare wires may extend outwards from the snare loop. The snare wires cooperate and join to form a snare loop 418 that may engage an underlying tissue, to resect tissue. In the illustrated embodiment, multiple spaced apart ring shaped elements 422 may be positioned around, and secured to different portions of the snare loop 418. The ring elements 422 may function as traction rings, and can be configured to increase traction during engagement of the snare loop 418 with the underlying tissue, in order to reduce slippage of the snare loop 418 over the tissue. In order to secure the ring elements 422 to different portions of the snare loop 418, multiple grooves or indentations may be provided on the snare loop 418 at those portions. Appropriate ways to attach and fixedly secure the ring elements 422 to the loop 418 include press-fitting, swaging, snap-fitting, etc. Further, though shown as extending across the entire length of the snare loop 418, the ring elements 422 may also be positioned to extend only partially around the snare loop, in order to enhance frictional engagement only at specific intended portions of the underlying tissue.

FIG. 4B shows a cross-sectional view of an exemplary ring element 422 that may be secured over the snare loop 418 shown in FIG. 4A. Though shown as being of a C-shaped structure, the ring element 422 may also have a different cross-section. The opening 422 (a) within the ring element 422 may facilitate securing the ring element 422 to the snare loop 418. Specifically, through the opening 422 (a), the ring element may be press-fitted, snapped on to, or crimped to the snare loop 418. Further, each ring element 422 may have a rough irregular outer surface, for example, a knurl, to enhance frictional engagement (i.e., to increase traction) of the snare loop to the tissue.

FIG. 4C is a partial perspective view showing the ring elements 422 configured to engage the snare loop 418. As mentioned earlier, the snare loop 418 may have multiple grooves or indentations provided over its peripheral surface, to facilitate attachment of the ring elements 422 to the snare loop. As shown, each ring element 422 may have a partially cylindrical cross-section at its front portion, to substantially surround the snare loop at a specific location. Further, the backwards cross-sectional structure of each ring element 422 may be tapered, and of a decreasing nature. This may facilitate easy retraction of the snare loop into the actuation member 406, without any obstruction being experienced due to the ring elements 422.

Figure 5:
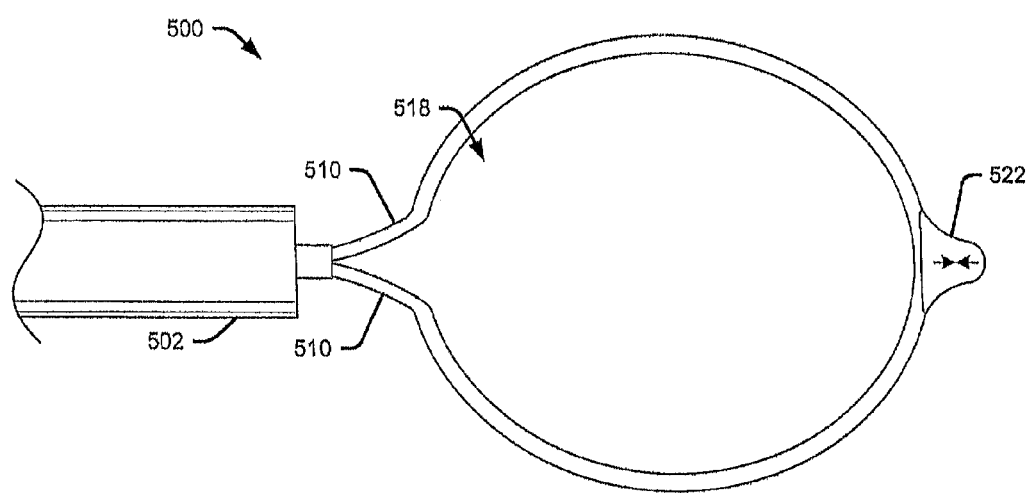
FIG. 5 shows a perspective view of a medical device for resecting tissue, in accordance with another embodiment of the disclosure.

FIG. 5 shows a medical device 500 for resecting tissue from a target site, where an auxiliary loop 522 may be provided at a distal tip of a larger snare loop 518. Similar to the embodiments described earlier, the larger loop 518 may be formed by snare wires 510 extending outward from an actuation member contained within an elongate shaft 502. The auxiliary loop 522 may engage a relatively smaller portion of an underlying tissue, to pinch and resect that portion. For example, as the auxiliary loop 522 is drawn closed, it may provide more traction or friction to the larger snare loop 518, enabling it to ensnare a larger portion of the tissue. Further, the provision of an auxiliary loop at a distal portion, or, any other peripheral portion of a larger snare loop, though explained in context of the current embodiment, may also be incorporated in any of the previously described embodiments. An additional actuation mechanism may be provided to actuate the auxiliary loop 522 independently. Further, in certain embodiments, both the larger loop 518 and the auxiliary loop 522 may be actuated through a common actuation mechanism.

In all the non-limiting embodiments described herein, materials used to manufacture the actuation member, the elongate shaft, the snare wires, and other components that may interact with portions of the human body, may include a rigid and/or a flexible material either in combination or alone. Additionally, exemplary materials may include metals, polymers, alloys, composite, or the like, either in combination or alone. In some embodiments, the material employed may include a self-expandable material such as a shape memory material, Nitinol, for example. Other suitable material may also be contemplated without departing from the scope and spirit of the disclosure.

Embodiments of the present disclosure may be applicable to any medical or non-medical procedure. In addition, certain aspects of the aforementioned embodiments may be selectively used in collaboration, or removed, during practice, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A tissue resection device, comprising:
an elongate shaft having a proximal end and a distal end;
an actuation member extending at least partially through the elongate shaft;
one or more snare wires extending through a lumen of the actuation member and emerging outwards from a distal portion of the actuation member;
a snare loop formed by the one or more snare wires, the snare loop being configured to engage tissue intended to be resected from a target site; and
a plurality of elements positioned over a peripheral surface of the snare loop, wherein each of the plurality of elements is a ring engaging and at least partially enclosing a portion of the peripheral surface of the snare loop, and each ring has an open-ended structure.

2. The tissue resection device of claim 1, wherein the snare loop has an expanded orientation and a retracted position, and wherein, in the retracted position, the snare loop is retracted into the actuation member.

3. The tissue resection device of claim 2, wherein, in the expanded orientation, the snare loop has one of an elliptical, a circular, an ovular, a square, a rectangular, a polygonal, and an irregular shape, overlaying the tissue.

4. The tissue resection device of claim 2, wherein in the expanded orientation of the snare loop, the one or more snare wires orient substantially perpendicular to a plane containing the tissue.

5. The tissue resection device of claim 1, wherein the snare loop has one of a plurality of grooves, striations, indentations, protrusions, and depressions provided over a peripheral portion thereof, and extending at least partially over a length of the snare loop.

6. The tissue resection device of claim 1, wherein at least one of the plurality of elements positioned over the peripheral surface of the snare loop, or the snare loop, has an irregular rough surface.

7. The tissue resection device of claim 1, wherein each of the rings is a C-shaped ring.

8. The tissue resection device of claim 1, wherein the rings are one of snap-fitted, press-fitted, and crimped to the snare loop, and have a slanting and decreasing cross-sectional rear structure, to facilitate smooth retraction of the snare loop into the actuation member.

9. The tissue resection device of claim 1, wherein each of the plurality of elements has an irregular surface configured to engage the tissue, the irregular surface being configured to cause friction between the tissue resection device and the tissue, for resection of the tissue.

10. A tissue resection device, comprising:
an elongate shaft having a proximal end and a distal end;
an actuation member extending at least partially through the elongate shaft, and being configured to reciprocate within the elongate shaft between a retracted position and an extended position; and
one or more snare wires extending through a lumen of the actuation member, emerging out from a distal portion of the actuation member;
wherein one or more spaced apart ring-shaped elements are positioned on the one or more snare wires, and each ring-shaped element includes a circumferential opening that completely separates a first end of the ring-shaped element from a second end of the ring-shaped element.

11. The tissue resection device of claim 10, wherein reciprocation of the actuation member moves the one or more snare wires between an expanded orientation and a retracted orientation within the elongate shaft, and wherein, in the extended position of the actuation member, the one or more snare wires are in the expanded orientation, and in the retracted position of the actuation member, the one or more snare wires retract into the elongate shaft into the retracted orientation.

12. The tissue resection device of claim 10, wherein the one or more snare wires have one of a plurality of grooves, striations, indentations, protrusions, and depressions provided over a peripheral portion thereof, and extending at least partially over a length of the one or more snare wires.

13. The tissue resection device of claim 10, wherein each ring-shaped element is C-shaped.

14. A tissue resection device, comprising:
an elongate shaft having a proximal end and a distal end;
an actuation member extending at least partially through the elongate shaft, and being configured to reciprocate within the elongate shaft between a retracted position and an extended position;
a snare loop formed by one or more snare wires extending through a lumen of the actuation member, the snare loop being configured to engage tissue intended to be resected from a target site; and
a plurality of structures positioned around different peripheral positions of the snare loop, wherein each of the plurality of structures extends from a first end toward a second end, is tapered radially inward from the second end toward the first end such that a cross-sectional dimension of each of the plurality of structures is greater at the second end than at the first end, is a ring engaging and at least partially enclosing a portion of a peripheral surface of the snare loop, and has an open-ended structure.

15. The tissue resection device of claim 14, wherein the snare loop has one of a plurality of grooves, striations, indentations, protrusions, and depressions provided over a peripheral portion thereof, and extending at least partially over a length of the snare loop.

16. The tissue resection device of claim 14, wherein each of the plurality of structures has an irregular rough surface.

17. The tissue resection device of claim 14, wherein each ring is C-shaped.

18. The tissue resection device of claim 14, wherein each ring is one of snap-fitted, press-fitted and crimped to the snare loop, and has a slanting and decreasing cross-sectional rear structure, to facilitate smooth retraction of the snare loop into the actuation member.

* * * * *